United States Patent [19]
Makino et al.

[11] Patent Number: 5,938,413
[45] Date of Patent: Aug. 17, 1999

[54] METHOD AND APPARATUS FOR PROTECTING A PUMP MECHANISM FROM EXTRANEOUS FLUID

[75] Inventors: Hideo Makino; Kenji Katayama; Yoshitaka Takeda, all of Akaiwa-gun, Japan

[73] Assignee: Alaris Medical Systems, Inc., San Diego, Calif.

[21] Appl. No.: 08/872,842

[22] Filed: Jun. 11, 1997

[51] Int. Cl.[6] .............................. F04B 43/12; F04B 43/08
[52] U.S. Cl. ............................. 417/474; 417/53; 604/153
[58] Field of Search ............................. 417/477.7, 477.1, 417/53, 474; 604/153

[56] References Cited

U.S. PATENT DOCUMENTS

| | | | |
|---|---|---|---|
| 5,165,874 | 11/1992 | Sancoff et al. | 417/474 |
| 5,499,906 | 3/1996 | O'Leary | 417/53 |
| 5,511,951 | 4/1996 | O'Leary | 417/53 |
| 5,513,957 | 5/1996 | O'Leary | 417/53 |
| 5,549,460 | 8/1996 | O'Leary | 417/474 |
| 5,660,529 | 8/1997 | Hill | 417/53 |
| 5,709,534 | 1/1998 | O'Leary | 417/53 |
| 5,716,194 | 2/1998 | Butterfield et al. | 417/43 |
| 5,741,121 | 4/1998 | O'Leary | 417/53 |

*Primary Examiner*—Charles G. Freay
*Assistant Examiner*—Paul L. Ratcliffe
*Attorney, Agent, or Firm*—Fulwider Patton Lee & Utecht, LLP

[57] ABSTRACT

A plurality of finger members disposed adjacent each other are moved by a driving mechanism in a reciprocal, sequential manner. Infusion is carried out when the finger members engage an infusion tube in a peristaltic sequence. The finger members contact each other by projections formed integrally on the upper and lower surfaces of the finger members to reduce the contact surface area. A fluid diversion guiding hole is contained in a tube-pressing portion of each finger member. The guide holes of adjacent finger members are aligned to form a continuous channel for discharging leaking infusion fluid. Bevels surround the guiding holes and are inclined toward the center of the hole. Each finger member also includes a rib that is integral with and protrudes upward from the upper surface of the finger member for blocking infusion fluid from the finger members and drive mechanism. In a preferred embodiment, the projections are linear and substantially parallel with the sides of the guiding hole which are, in turn, parallel with the movement of the tube-pressing portion.

30 Claims, 4 Drawing Sheets

METHOD AND APPARATUS FOR PROTECTING A PUMP MECHANISM FROM EXTRANEOUS FLUID

BACKGROUND OF THE INVENTION

The invention relates generally to pump mechanisms, and more particularly, to a method an apparatus for protecting a pump mechanism used in an infusion pump from possible adverse effects caused by the entrance of extraneous fluid into the pump mechanism, such as adhesion of mechanism parts.

An infusion system typically includes a reservoir, such as a bottle or bag, for holding infusion fluid, a drip chamber for monitoring the flow of fluid from the reservoir, infusion tubing for carrying the fluid to an injection needle, and an infusion pump for precisely controlling the flow rate of fluid through the infusion tubing. One conventional infusion pump, known as a linear peristaltic pump, comprises finger members that move into and out of contact with the tubing in a peristaltic manner so that they compress the infusion tube in a wavelike motion, squeezing the fluid as the wave progresses and thereby carry out the infusion. The finger members and the drive mechanism controlling the movement of the finger members are collectively referred to as a pump mechanism. The pump mechanism and a control processor with ancillary power and display systems comprises an infusion pump. A typical infusion pump as such is described in Japanese patent publication No. Sho-62-8763.

In some cases during operation, infusion fluid, such as a liquid containing a sugar, leaks out of the bottle or bag and travels down the outer surface of the infusion tube and may enter the pump mechanism area. If the pump is constructed so that leaking infusion fluid is not diverted out of the pump, the leaking infusion fluid may accumulate in the pump mechanism, dry, and adhere to the pump mechanism and cause the finger members to stick to the driving mechanism and to each other. This sticking can cause the pump mechanism to malfunction and not be available when needed.

In a typical infusion pump, adjacent finger members contact each other in a face-to-face manner, i. e., the upper and lower surfaces of the finger members rub against each other as the finger members move. As infusion fluid accumulates on the face-to-face surfaces of the finger members and begins to dry, the finger members may stick to each other and a malfunction of the pump mechanism may occur if the driving mechanism does not have sufficient power to overcome the adhesion of the fingers to one another. A remarkably large force may be required, depending on the nature of the leaking fluid, to break the face-to-face adhesive bond. This is especially so when an attempt is made to break the bond by moving the finger members in the direction parallel to the face, which is the direction of movement during pump operation.

One method to eliminate this adhesive problem involves covering, with a rubber sheet, the portion of the finger members which compresses the infusion tube. Essentially the rubber sheet blocks infusion fluid from entering the pump mechanism. However, as the rubber sheet is continuously pressed against the infusion tube by the finger members, the rubber sheet may become swelled by the plasticizer from the infusion tube and may become soft and eventually break. Accordingly, the rubber sheet must be periodically replaced.

A second method involves making the clearances between the finger members as narrow as possible so that infusion fluid is unlikely to enter the pump mechanism. To further ensure that fluid does not enter, a grease like repellent filler such as silicon may be placed in the clearances. There is, however, a limitation in the mechanical accuracy, and it is very difficult to completely block the entrance of infusion fluids. In addition, an upgrading of the mechanical accuracy results in higher production costs. Furthermore, when a repellent filler is used, there is a possibility that the filler may leak into other regions of the pump mechanism and a pump mechanism malfunction may result.

A third method involves unitizing a cleanable and removable pump mechanism. When infusion fluid adheres to the inside of the pump mechanism, the unitary pump mechanism may be removed, cleaned and reinstalled. In unitary pump mechanisms, however, the mechanical connection is often times loose and produces high noise levels during operation. Furthermore, it is inconvenient for a nurse, who is very busy with daily business, to remove and wash the pump mechanism.

Hence, those skilled in the art have recognized a need for a pump mechanism that conveniently and effectively reduces or eliminates the entrance of infusion fluid into the pump mechanism and reduces the detrimental effects of any fluid which does enter the pump mechanism. The invention fulfills these needs and others.

SUMMARY OF THE INVENTION

Briefly, and in general terms, the invention is directed to an apparatus and a method that protects a pump mechanism from the detrimental effects typically associated with the accumulation of leaking fluids within the pump mechanism.

In one aspect, the invention comprises a finger member for use in a pump mechanism having a plurality of reciprocating finger members disposed for sequentially engaging an infusion tube to move fluid through the tube in a peristaltic manner. The pump mechanism also has a drive mechanism for moving the finger members. Each finger member includes an upper and a lower surface and a plurality of projections protruding from the upper and lower surfaces. The finger members are disposed so that the projections will be aligned with and will engage the projections of the adjacent fingers.

In another aspect, the invention comprises a pump mechanism for moving fluid through an infusion tube. The pump mechanism includes a plurality of finger members, each finger member having a tube-pressing portion and upper and lower surfaces. Also included is a plurality of projections protruding from the upper and lower surfaces of each finger member. The finger members are disposed so that the projections of adjacent finger members are substantially aligned with each other and contact each other. Further included is a drive mechanism for moving the finger members in a peristaltic manner so that the tube-pressing portions sequentially engage the infusion tube.

In yet another aspect, the invention comprises a method for protecting a pump mechanism from adhesion caused by the entry of extraneous fluid into the pump mechanism. The pump mechanism has a plurality of reciprocating finger members adjacently disposed for sequentially engaging an infusion tube to move fluid through the tube in a peristaltic manner. The pump mechanism also has a drive mechanism for moving the finger members and each finger member has upper and lower surfaces. The method includes the step of limiting the surface-area contact between adjacent upper and lower surfaces. Also included is the step of forming a continuous channel that is associated with each finger member. Further included is the step of diverting the fluid from the upper and lower surfaces toward and into the channel.

These and other aspects and advantages of the present invention will become apparent from the following more detailed description, when taken in conjunction with the accompanying drawings which illustrate, by way of example, the preferred embodiments of the invention.

DETAILED DESCRIPTION OF PREFERRED EMBODIMENTS

Figure 1:
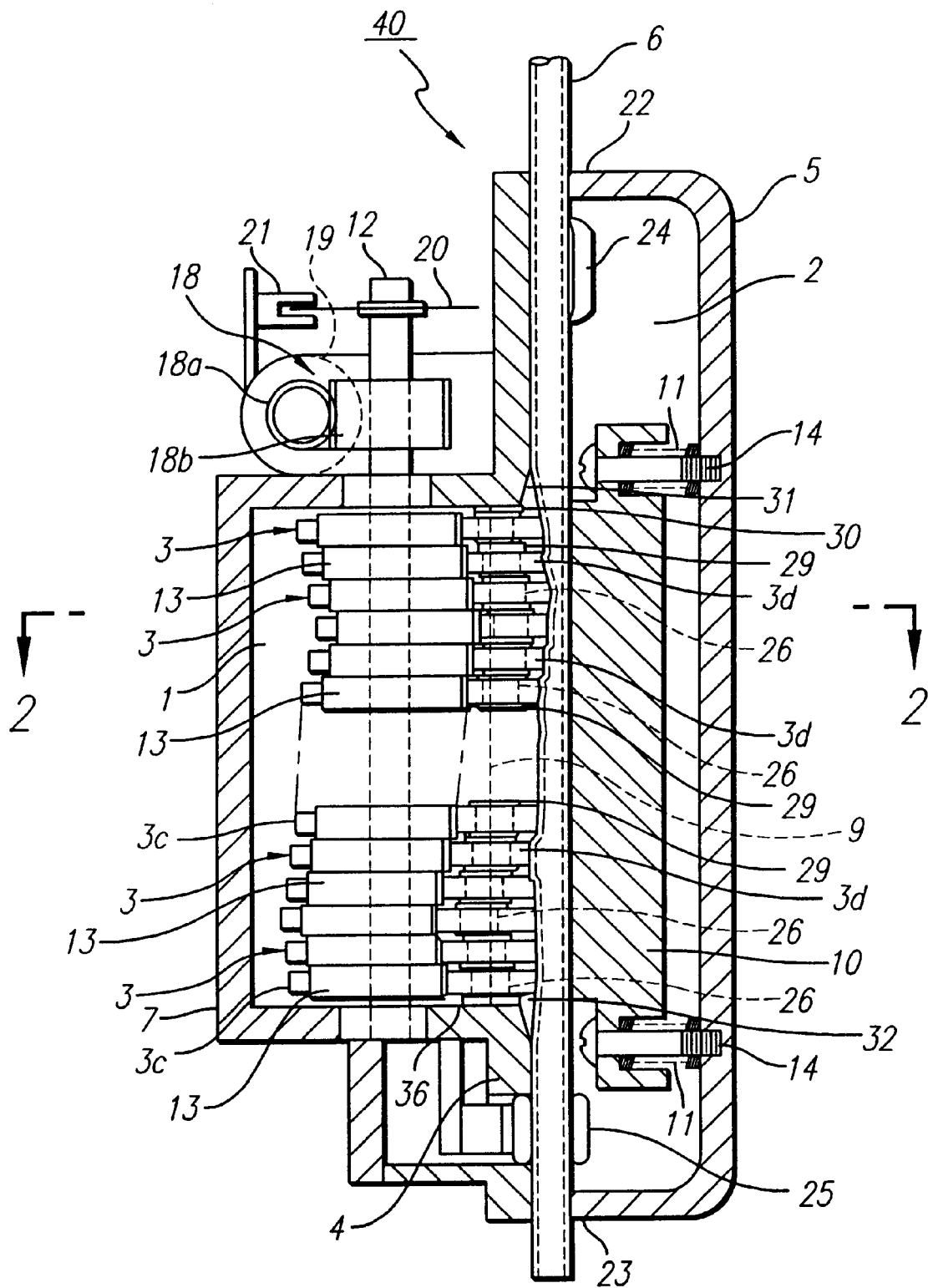
FIG. 1 is a longitudinal-sectional view showing an infusion pump according to a preferred embodiment of the invention.
Figure 2:
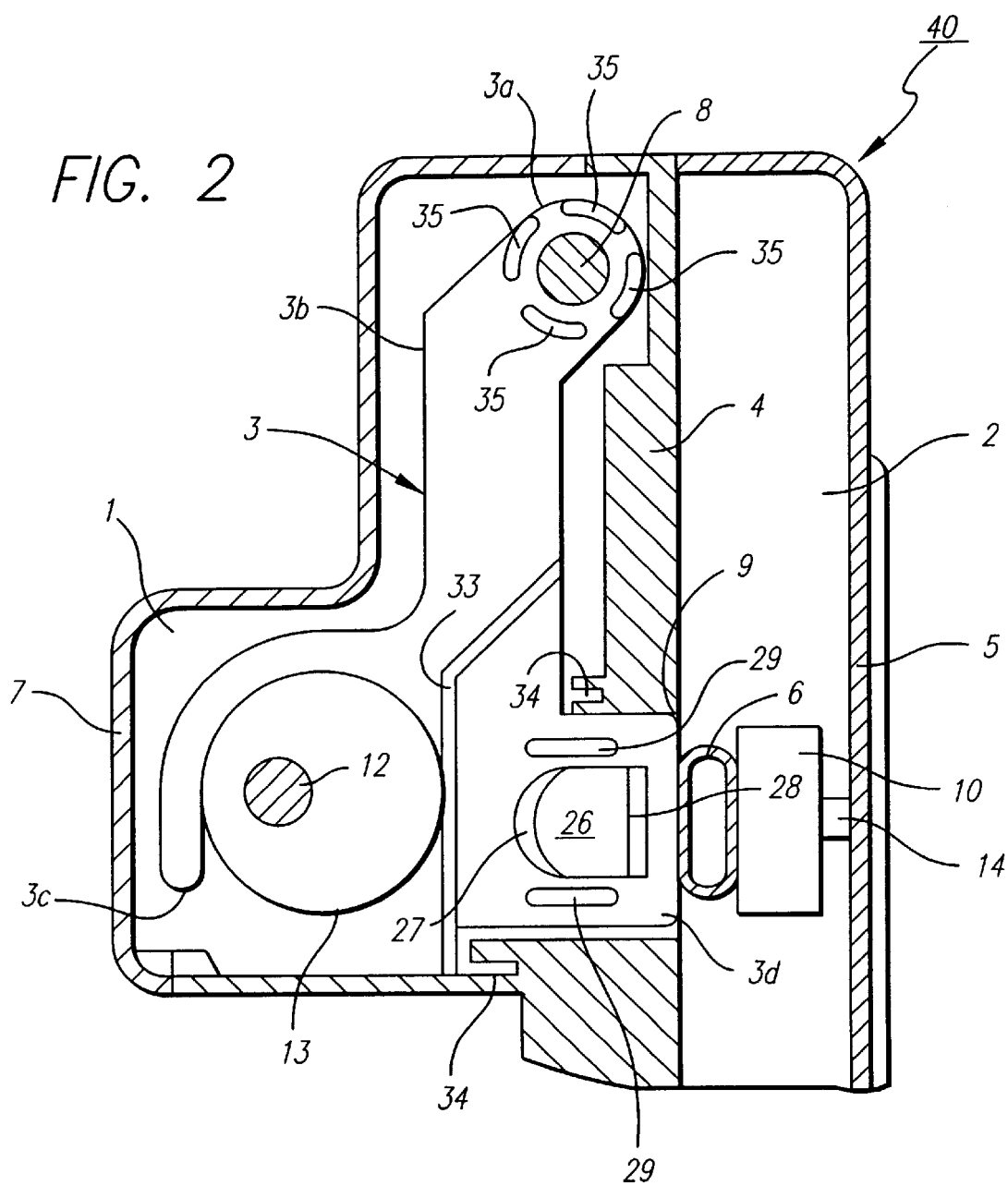
FIG. 2 is an enlarged cross-sectional view taken along the line 2—2 in FIG. 1.

Turning now to the drawings with more particularity, in FIGS. 1 and 2 there is shown a linear peristaltic infusion pump 40 in accordance with an embodiment of the invention. The infusion pump 40 is equipped with a mechanism chamber 1 which is defined by a cover 7 at the rear and a partition 4. Housed within the mechanism chamber 1 are a plurality of movable finger members 3 disposed in an adjacent fashion. A pump chamber 2, adjacent the mechanism chamber 1, is defined by the partition 4 and an openable and closable lid 5.

The preferred embodiment of the infusion pump 40 described herein is configured so that the finger members 3 move in a substantially horizontal direction, as is typical with many infusion pumps. Some pumps, however, may have finger members 3 that move in other directions. Furthermore, in the preferred embodiment the finger members 3 are stacked in a substantially vertical manner, although other configurations may be possible.

Each finger member 3 includes a supporting portion 3a that is pivotally supported relative to a pivotal axis 8. The pivotal axis 8 is installed in the vertical direction in the mechanism chamber 1. An arm 3b extends horizontally along the partition 4 from the supporting portion 3a while a U-shaped cam-holding portion 3c projects from the arm 3b. A tube-pressing portion 3d projects toward the partition 4 from the cam-holding portion 3c. The tube-pressing portion 3d communicates with the pump chamber 2 through an opening 9 contained within the partition 4.

A pressure plate 10 is attached to the lid 5 by a plurality of bolts 14. Concentric with each bolt is a spring 11. The bolts 14 movably support the pressure plate 10 while the springs 11 bias the pressure plate 10 away from the lid 5. Positioned between the pressure plate 10 and the finger members 3 and aligned with an opening 9 is an infusion tube 6. During operation, the pressure plate 10 and the accompanying force provided by the springs 11 provide the force necessary to hold the infusion tube 6 in place.

A plurality of eccentric cams 13, one for each finger member 3, are stacked on a rotatable drive shaft 12 and are aligned and positioned within the cam-holding portion 3c. The eccentric cams 13 rotate together with the drive shaft 12. The finger members 3 are constructed so as to carry out peristaltic movements in line with the rotation of the drive shaft 12 and the eccentric cams 13. This motion results in substantially horizontal movements of the tube-pressing portion 3d centering around the pivotal axis 8 of the finger members 3. The infusion tube 6 is pressed, in turn, between the tube-pressing portion 3d and the pressure plate 10 so as to transfer the infusion fluid downward toward the injection needle (shown in FIG. 5).

The upper end of the driving shaft 12 is connected to a motor 19 by way of a transmission mechanism 18. The transmission mechanism 18 includes a worm gear 18a; engaged with the worm gear 18a is a gear 18b. The motor 19, transmission mechanism 18, drive shaft 12 and eccentric cams 13 constitute a drive mechanism for peristaltically moving the finger members 3. An encoder 20 is attached to the driving shaft 12 while a rotation position detector 21 is aligned with the encoder 20. A guide 24 for aligning the infusion tube 6 and a pinch-off means 25 to pinch the pump outlet of the infusion tube 6 are provided.

Figure 4:
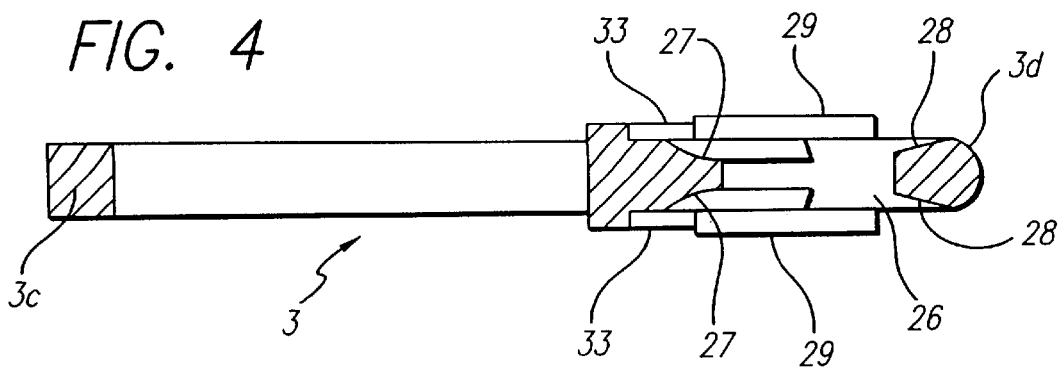
FIG. 4 is an enlarged cross-sectional view of a finger member used in an infusion pump according to a preferred embodiment of the invention.
Figure 3:
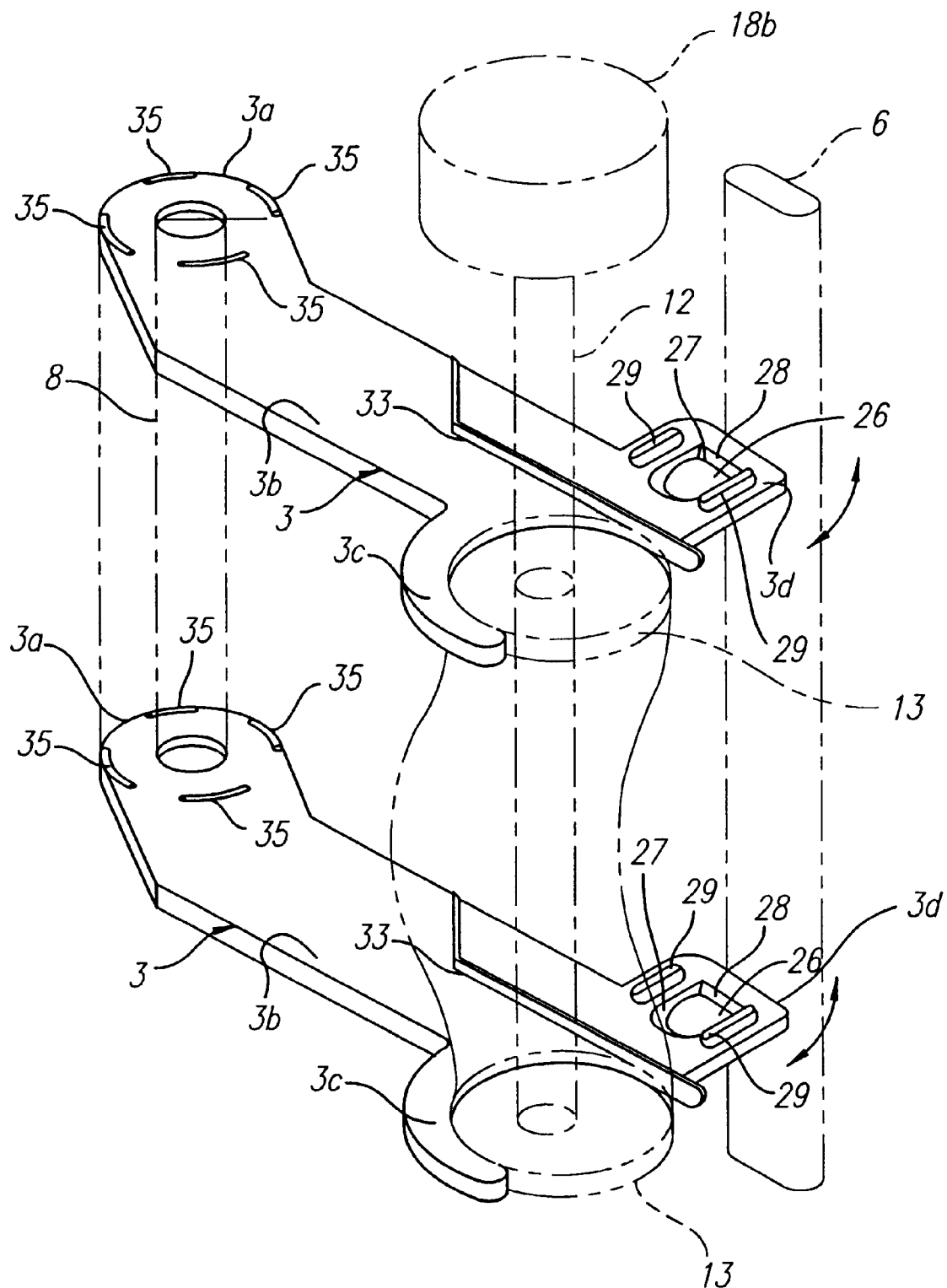
FIG. 3 is a perspective view showing the finger members used in an infusion pump according to a preferred embodiment of the invention.

In a preferred embodiment as shown in FIGS. 3 and 4, the tube-pressing portion 3d has a guiding hole 26 which passes therethrough in the substantially vertical direction. The size and alignment of the guiding holes 26 are such that during horizontal movement of the tube-pressing portions 3d the guiding holes 26 form a continuous channel that runs from the extreme upper finger member 3 to the extreme lower finger member 3. The vertical channel formed by the general alignment of the guiding holes 26 provides a path for infusion fluid, which may accumulate on the upper surfaces of the finger members 3, to travel and thereby be discharged outside the pump without adhering to the finger members or entering the drive mechanism. Therefore, the accumulation of infusion fluid is prevented and the possibility of finger members 3 sticking to each other is greatly reduced.

The guiding holes 26 are made large enough so that even when a finger member 3 has been moved into contact with the tubing, its guiding hole will still have some overlap with the guiding holes of the adjacent finger member.

The tube-pressing portion 3d also includes bevels 27, 28 that incline toward the center of the guiding hole 26 and are provided on both the upper and lower surfaces of the tube-pressing portion 3d. The bevels 27, 28 tend to divert infusion fluid which enters the tube-pressing portion 3d toward the guiding hole 26. In an alternate embodiment the bevels 27, 28 are provided only at the upper surface of the tube-pressing portion 3d.

A pair of projections 29 are formed integrally on both the upper and lower surfaces of the tube-pressing portion 3d. Preferably, these projections 29 are linear and are substantially parallel with the sides of the guiding hole 26 and are substantially parallel with the horizontal movement of the tube-pressing portion 3d. The linear projections 29 of vertically adjacent finger members 3 are in contact with each other and remain so even during the peristaltic movement of the finger members 3. This keeps the finger members 3 in a linear contacted state, even during horizontal movement, and thereby provides a continuous guide for diverting infusion fluid as well as a substantially reduced surface area of contact between adjacent fingers.

Each linear projection 29 is positioned between an edge of the tube-pressing portion 3d, which is substantially parallel with the horizontal movement of the tube-pressing portion, and a side of the guiding hole 26, which is also substantially parallel with the horizontal movement of the tube-pressing portion. Accordingly, infusion fluid is directed toward the guiding hole 26 by the projections, and each projection limits fluid from flowing over the edges of the tube-pressing portion 3d.

As shown in FIG. 1, a pair of upper linear projections 30 is integrally formed on the upper opening-facing side of the partition 4 at the opening 9 and protrude downward. Likewise, a pair of lower linear projections 36 are integrally formed on the lower opening-facing sides of the partition 4 at the opening 9 and protrude upward. The linear projections 29 of the extreme upper and lower finger members 3 contact the upper linear projections 30 and the lower linear projection 36, respectively. An upper guide groove 31 and a lower guide groove 32 are provided on the pump-chamber-facing side of the partition 4. The guide grooves 31, 32 incline toward the mechanism chamber 2 and thereby aid in diverting infusion fluid down along the infusion tube 6 and out the infusion pump 40. The upper guide groove 31 assists in diverting or channeling the leaking fluid through the guiding holes 26 in the finger members 3 while the lower guide groove 32 diverts or channels the leaking fluid back to the fluid tubing so that it leaves the pump 40.

A weir-like rib 33, as shown in FIG. 3, is integrally formed on the upper and lower surfaces of each finger members 3. The height of the rib 33 is less than the linear projection 29 so that the ribs 33 of adjacent finger members 3 do not contact each other during the horizontal movement of the finger members 3. The ribs 33 nevertheless prevent infusion fluid from flowing to the support portion 3a, arm 3b and cam-holding portion 3c of the finger member 3. The ribs 33 retain the fluid in the region surrounding the guiding hole 26 and thereby protect the portions of the finger members 3 that interface with the drive mechanism from exposure to leaking fluid and from adhering to each other were that fluid to dry on those portions. The ribs 33 also tend to divert the fluid toward the guiding holes 26 so that it flows downward and away from the mechanism.

The vertical grooves 34 as shown in FIG. 2, are formed in the surface of the partition 4 facing the mechanism at both edges of the partition 4 near the opening 9. The vertical grooves 34 channel infusion fluid, which may be present on the upper surface of the finger members 3, downward and out of the infusion pump 40.

A plurality of supporting projections 35, substantially equidistant from the pivotal axis 8, are integrally formed on the upper and lower surfaces of the pivotally supporting portion 3a of the finger members 3. The supporting projections 35 of adjacent finger members 3 are in contact with each other. The supporting projections 35 have the same height as the linear projection 29, thereby allowing the horizontal posture of the finger members 3 to be maintained.

Figure 5:
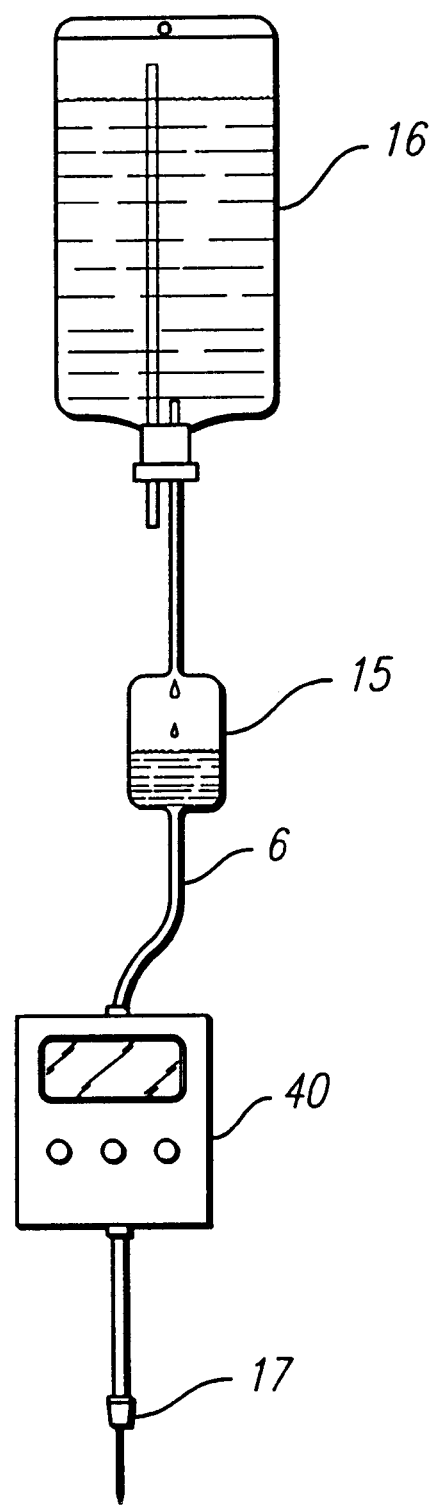
FIG. 5 is a rough side plan view showing a use state of an infusion pump according to a preferred embodiment of the invention.

In operation, an infusion tube 6, as shown in FIG. 5, in which an infusion fluid flows down from a drip chamber 15, is gradually compressed from upward to downward by the tube-pressing portion 3d of the finger members 3 which are peristaltically driven by the rotating eccentric cams 13, thereby causing the infusion fluid to be sent to the injection needle 17. The eccentric cams 13 are rotated by a drive shaft 12 which is driven by the motor 19. Although not shown, additional support would be provided to the infusion fluid bottle 16, such as by a portable pole hanging apparatus. The bottle 16 is connected to the infusion tube 6 through the drip chamber 15 at the upstream end of the infusion tube 6.

Should some infusion fluid leak from the infusion fluid bottle 16, it may travel along the outer surface of the infusion tube 6 and enter the infusion pump 40. If protection against such fluid were not present, the leaking fluid may accumulate on the tube-pressing portion 3d of the fingers 3 and dry. It is well known that the greater the surface area to which adhesive is applied, the greater force is required to break the adhesive bond. Generally, the adhesive force between two objects is lessened in a point-to-point, line-to-line, point-to-face, or line-to-face contact. Sufficient adhesive strength will not exist and the objects can be more easily separated. Given the line-to-line contact as provided by the small linear projections 29 between adjacent tube-pressing portions 3d of the finger members, the adhesive bond of any dried infusion fluid will be relatively weak. This weak bond is more easily broken as the finger members 3 are urged into their peristaltic movement by the driving shaft 12. Accordingly, any sticking of the finger members 3 is overcome and a smooth, continuous peristaltic motion is maintained.

Any infusion fluid which may accumulate on the tube-pressing portion 3d of the finger members 3 is diverted toward the guiding hole 26 by the bevels 27, 28 and once inside the guiding hole 26, the fluid is diverted downward through adjacent guiding holes 26 in adjacent finger members 3 and is discharged through the lower guide groove 32. In some cases the quantity of infusion fluid which enters the tube-pressing portion 3d of the finger portion 3 is too great and does not flow downward through the guiding holes 26. In this case, the rib 33 blocks the flow of infusion fluid into the cam-holding portion 3c and the drive mechanism and the fluid is diverted toward the vertical grooves 34 and is thereby guided downward and out the infusion pump 40.

Therefore, not only does the protective apparatus in accordance with the invention protect the driving mechanism from leaking fluid from the tubing or elsewhere, the apparatus also provides reduced-size contact surfaces between adjacent moving fingers so that any adherence between those fingers can be overcome by the driving mechanism. The projections in accordance with the invention present a much lowered surface area for such fluid. This results in a weaker bond that can be more easily broken by the driving mechanism. Greater mechanical accuracy is not required thus leading to lowered manufacturing costs. Rubber sheets, with their attendant expense, are also not needed.

The projections on the fingers that not only provide the reduced-sized contact surfaces also tend to divert leaking fluid that may interfere with the correct operation of the pumping mechanism to a specifically designed fluid channel that will guide such fluid out of the pump. Additional channels are provided for moving leaking fluid away from the fingers and the other parts of the driving apparatus. Furthermore, the driving mechanism need not be removable for cleaning thus permitting the efficiency of a permanently mounted mechanism. Lower noise levels can be designed as well as lower manufacturing costs due to this mounting arrangement.

In the above description, a preferred embodiment of the invention is incorporated in an infusion pump. The invention, however, is also applicable to other mechanisms in which extraneous fluid may enter and interfere with the operation of the mechanism.

While several particular forms of the invention have been illustrated and described, it will be apparent that various modifications can be made without departing from the spirit and scope of the invention. Accordingly, it is not intended that the invention be limited, except as by the appended claims.

What is claimed is:

1. A pump mechanism for moving fluid through an infusion tube, the pump mechanism comprising:

a plurality of finger members, each finger member having a tube-pressing portion and upper and lower surfaces;

a plurality of projections protruding from the upper and lower surfaces of each finger member, wherein the finger members are disposed so that the projections of adjacent finger members are substantially aligned with each other and contact each other; and a drive mechanism for moving the finger members in a peristaltic manner so that the tube-pressing portions sequentially engage the infusion tube.

2. The pump mechanism of claim 1 wherein the projections are substantially parallel with the movement of the tube-pressing portion, as moved by the drive mechanism.

3. The pump mechanism of claim 2 wherein the lengths of the projections are such that the projections of adjacent finger members maintain contact during the complete movement range of the finger members.

4. The pump mechanism of claim 3 wherein the finger members are substantially vertically disposed and the finger members move in a substantially horizontal fashion.

5. The pump mechanism of claim 1 wherein each finger member has a guiding hole through which fluid may flow and the guiding holes are sized and aligned with each other such that a continuous channel is formed and maintained during the complete movement range of the finger members.

6. The pump mechanism of claim 5 further comprising a bevel on the upper surface of the finger member, wherein the bevel inclines toward the center of the guiding hole.

7. The pump mechanism of claim 6 further comprising a bevel on the lower surface of the finger member, wherein the bevel inclines toward the center of the guiding hole.

8. The pump mechanism of claim 7 wherein the guiding hole and the bevel is located in the tube-pressing portion of the finger member.

9. The pump mechanism of claim 5 wherein the projections are linear and are positioned between the sides of the guiding hole which are parallel with the movement of the tube-pressing portion and the edges of the tube-pressing portion which are parallel with the movement of the tube-pressing portion.

10. The pump mechanism of claim 5 wherein each finger member has a rib protruding upward from the upper surface and a rib protruding downward from the lower surface, the ribs for isolating the tube-pressing portion from the remaining portions of the finger member.

11. A finger member for use in a pump mechanism having a plurality of reciprocating finger members disposed for sequentially engaging an infusion tube to move fluid through the tube in a peristaltic manner, the pump mechanism further having a drive mechanism for moving the finger members, each finger member comprising:

an upper and a lower surface; and a plurality of projections protruding from the upper and lower surfaces and disposed so that the projections will be aligned with and will engage the projections of adjacent finger members.

12. The finger member of claim 11 wherein the projections are substantially parallel with the movement of the finger member, as moved by the drive mechanism.

13. The finger member of claim 12 wherein the lengths of the projections are such that the projections of adjacent upper and lower surfaces maintain contact during the complete movement range of the finger members.

14. The finger member of claim 11 further comprising a the tube-pressing portion having a guiding hole through which fluid may flow, wherein the guiding hole is sized and disposed such that it will be aligned with adjacent finger members to form a continuous channel and will maintain that channel during the complete movement range of the finger members.

15. The finger member of claim 14 further comprising means for diverting fluid toward the guiding hole.

16. The finger member of claim 15 wherein the diverting means comprises a plurality of bevels on the upper surface, wherein the bevels incline toward the center of the guiding hole.

17. The finger member of claim 16 wherein the diverting means further comprise a plurality of bevels on the lower surface, wherein the bevels incline toward the center of the guiding hole.

18. The finger member of claim 15 wherein the diverting means comprises a rib protruding upward from the upper surface for isolating the tube-pressing portion from the remaining portions of the finger member.

19. The finger member of claim 18 wherein the diverting means further comprises a rib protruding downward from the lower surface for isolating the tube-pressing portion from the remaining portions of the finger member.

20. The finger member of claim 14 wherein the projections are linear and are positioned between the sides of the guiding hole which are parallel with the movement of the finger member and the edges of the tube-pressing portion which are parallel with the movement of the finger member.

21. An infusion pump for moving fluid through an infusion tube, the infusion pump comprising:

a plurality of vertically disposed and movable finger members, each finger member having a tube-pressing portion and upper and lower surfaces, wherein each tube pressing portion has a guiding hole and the guiding holes are sized and aligned with each other such that a continuous channel is formed and maintained during the complete movement range of the finger members;

a plurality of bevels on the upper and lower surfaces, wherein the bevels incline toward the center of the guiding hole;

a drive mechanism for horizontally moving the finger members in a peristaltic manner so that the tube-pressing portions sequentially engage the infusion tube;

a plurality of linear projections protruding from the upper and lower surfaces of each finger member and positioned to be substantially parallel with the movement of the tube-pressing portion, wherein the finger members are disposed so that the linear projections of adjacent finger members are substantially aligned with and contact each other and the linear projections are sized to maintain contact during the complete movement range of the finger members;

a mechanism chamber for housing the finger members;

a pump chamber for housing the infusion tube; and a partition positioned between the mechanism chamber and the pump chamber and having an opening through which the finger members interface with the infusion tube, the partition having a pair of upper linear projections protruding downward from the upper opening-facing surface of the partition and having a pair of lower linear projections protruding upward from the lower opening-facing surface of the partition, wherein the upper and lower linear projections are substantially aligned with and contact the linear projections of the respective extreme upper and lower finger members.

22. The pump mechanism of claim 22 wherein each finger member has a rib protruding upward from the upper surface for isolating the tube-pressing portion from the remaining portions of the finger member and the height of the rib is less than the height of the linear projections.

23. The pump mechanism of claim 22 wherein:
    each finger member is pivotally disposed and has a pivotally supporting portion contiguous with the tube-pressing portion; and
    each finger member has a plurality of support projections protruding from the upper and lower surfaces of the pivotally supporting portion, the support projections being substantially the same height as the linear projections.

24. The pump mechanism of claim 22 wherein the pump-chamber-facing surface of the partition has an upper guide groove and a lower guide groove that incline toward the mechanism chamber.

25. The pump mechanism of claim 25 wherein the mechanism-chamber-facing surface of the partition has a plurality of vertical grooves located near the opening.

26. A method for protecting a pump mechanism from adhesion caused by the entry of extraneous fluid into the pump mechanism, the pump mechanism having a plurality of reciprocating finger members adjacently disposed for sequentially engaging an infusion tube to move fluid through the tube in a peristaltic manner, the pump mechanism further having a drive mechanism for moving the finger members, each finger member having upper and lower surfaces, the method comprising the steps of:
    limiting the surface-area contact between adjacent upper and lower surfaces;
    forming a continuous channel that is associated with each finger member; and
    diverting the fluid from the upper and lower surfaces toward and into the channel.

27. The method of claim 27 wherein the step of limiting the surface-area contact between adjacent upper and lower surfaces comprises the step of forming projections on the upper and lower surfaces of adjacent finger members so that they are aligned with each other and contact each other during the complete movement range of the finger members.

28. The method of claim 27 wherein the step of forming a continuous channel comprises the step of forming a guiding hole in each finger member, the guiding holes of adjacent finger members being sized and aligned with each other to form a continuous channel during the complete movement range of the finger members.

29. The method of claim 29 wherein the step of diverting the fluid from the upper and lower surfaces toward and into the channel comprises the step of forming bevels on the upper and lower surfaces of the finger member, the bevels inclining toward the center of the guiding hole.

30. The method of claim 30 wherein the step of diverting the fluid from the upper and lower surfaces toward and into the channel further comprises the step of forming a rib that protrudes upward from the upper surface and a rib that protrudes downward from the lower surface and the ribs for retaining the fluid in the portion of the finger member surrounding the guiding hole.

* * * * *

UNITED STATES PATENT AND TRADEMARK OFFICE
CERTIFICATE OF CORRECTION

PATENT NO. : 5,938,413
DATED : Aug. 17, 1999
INVENTOR(S) : Hideo Makino, Kenji Katayama, Yoshitaka Takeda It is certified that error appears in the above-identified patent and that said Letters Patent is hereby corrected as shown below:

Column 8, claim 22, line 66, change "22", to read --21--.

Column 9, claim 23, line 4, change "22", to read --21--.

Column 9, claim 24, line 13, change "22", to read --21--.

Column 9, claim 25, line 17, change "25", to read --24--.

Column 10, claim 27, line 5, change "27", to read --26--.

Column 10, claim 28, line 11, change "27", to read --26--.

Column 10, claim 29, line 17, change "29", to read --28--.

Column 10, claim 30, line 22, change "30", to read --29--.

Signed and Sealed this

First Day of February, 2000

Attest:

Q. TODD DICKINSON

*Attesting Officer*     *Acting Commissioner of Patents and Trademarks*